US012778408B2

(12) United States Patent
Molnar

(10) Patent No.: US 12,778,408 B2
(45) Date of Patent: Nov. 3, 2026

(54) STYLET AND BOUGIE DEVICE

(71) Applicant: WM & DG, Inc., Deerfield, IL (US)

(72) Inventor: Robert W. Molnar, Bannockburn, IL (US)

(73) Assignee: WM & DG, Inc., Northbrook, IL (US)

( * ) Notice: Subject to any disclaimer, the term of this patent is extended or adjusted under 35 U.S.C. 154(b) by 159 days.

(21) Appl. No.: 17/950,305

(22) Filed: Sep. 22, 2022

(65) Prior Publication Data

US 2023/0088652 A1 Mar. 23, 2023

Related U.S. Application Data

(60) Provisional application No. 63/247,463, filed on Sep. 23, 2021.

(51) Int. Cl.

*A61M 16/04* (2006.01)
*A61B 1/00* (2006.01)
*A61B 1/267* (2006.01)

(52) U.S. Cl.

CPC .......... *A61B 1/267* (2013.01); *A61B 1/00154* (2013.01); *A61M 16/0434* (2013.01)

(58) Field of Classification Search

None
See application file for complete search history.

(56) References Cited

U.S. PATENT DOCUMENTS 4,351,330 A * 9/1982 Scarberry ............ A61N 1/0517 607/124
4,571,239 A * 2/1986 Heyman ........... A61M 25/0017 604/915
5,066,285 A * 11/1991 Hillstead ........... A61M 25/0662 600/585
5,595,172 A * 1/1997 Reese ............... A61M 16/0484 128/207.14
5,603,703 A * 2/1997 Elsberry ............ A61B 17/3401 604/523
5,665,052 A * 9/1997 Bullard ............ A61M 16/0488 600/187
8,746,239 B2 * 6/2014 Yoshida ................ A61M 16/04 128/207.14
9,357,905 B2 6/2016 Molnar et al.
9,415,179 B2 8/2016 Molnar
9,918,618 B2 3/2018 Molnar
10,279,136 B2 5/2019 Molnar
10,342,944 B2 7/2019 Molnar
10,368,726 B2 * 8/2019 Perez-Lizano ......... A61B 1/267
10,653,307 B2 5/2020 Molnar
10,722,110 B2 7/2020 Molnar
11,051,682 B2 7/2021 Molnar
(Continued)

OTHER PUBLICATIONS

PCT Notification of Transmittal of the International Search Report and Written Opinion dated Jan. 11, 2023 for PCT Application No. PCT/US22/44342.

*Primary Examiner* — LaToya M Louis
(74) *Attorney, Agent, or Firm* — Greer, Burns & Crain, Ltd.

(57) ABSTRACT

A stylet having a channel configured as a drug-delivery and suction channel, as well as for housing a bougie and a camera. A system including the stylet and bougie device for guided placement of an endotracheal tube in the trachea. Intubation methods in which placement of an endotracheal tube is guided with the stylet/bougie device.

19 Claims, 6 Drawing Sheets

(56) References Cited

U.S. PATENT DOCUMENTS

| | | | | |
|---|---|---|---|---|
| 11,147,442 | B2 | 10/2021 | Molnar | |
| 11,202,561 | B2 | 12/2021 | Molnar | |
| 2011/0120458 | A1* | 5/2011 | Schwartz ............... | A61B 1/267<br>128/200.26 |
| 2013/0211263 | A1 | 8/2013 | Boedeker | |
| 2015/0258295 | A1 | 9/2015 | Stocking et al. | |
| 2017/0209022 | A1 | 7/2017 | Molnar | |
| 2020/0054849 | A1 | 2/2020 | Venticinque | |
| 2020/0113427 | A1 | 4/2020 | Molnar | |
| 2020/0114105 | A1 | 4/2020 | Molnar | |
| 2020/0139081 | A1 | 5/2020 | Gardner | |
| 2020/0237204 | A1 | 7/2020 | Molnar | |
| 2021/0299383 | A1 | 9/2021 | Molnar | |
| 2022/0110514 | A1 | 4/2022 | Molnar | |

* cited by examiner

STYLET AND BOUGIE DEVICE

CROSS-REFERENCE TO RELATED APPLICATIONS

This application claims the benefit of priority from U.S. Provisional Patent Application 63/247,463 filed Sep. 23, 2021, the entire disclosure of which is herein incorporated by reference in its entirety.

TECHNICAL FIELD

This disclosure relates to the field of medical devices, including medical devices for managing a patient airway and intubation methods.

BACKGROUND

Endotracheal intubation may need to be performed in medical emergency, e.g., a facial trauma, and/or during certain surgical procedures, in general anesthesia and/or under other circumstances when a patient cannot breathe unassisted and requires mechanical ventilation.

During endotracheal intubation, a healthcare professional may need to lift the epiglottis from the glottic opening in order to permit insertion of an endotracheal tube into the trachea and then position the endotracheal tube through the vocal cords.

Various instruments can be used in facilitating access to the trachea and positioning an endotracheal tube, including a stylet or a bougie. Each of the instruments has a different structure and function. A conventional bougie is a solid rod sufficiently flexible in order to be used for guiding insertion of an endotracheal tube by manipulating the epiglottis and tissues. In contrast, a stylet is typically made of some sturdy material, e.g., a metal, and is used as a backbone insertable into and removable form the endotracheal tube in order to provide a structural support to the endotracheal tube during insertion. With conventional stylets and bougies, a healthcare professional is typically limited to using either a bougie or a stylet, but not both at the same time.

However, there remains a need in the field for a stylet that can be used simultaneously with a bougie, if needed.

SUMMARY

This disclosure helps in addressing this need and provides a stylet that can be used in combination with a bougie for guided and expeditious placement of an endotracheal tube during intubation.

In one aspect, this disclosure relates to a stylet having a channel for housing a bougie, a camera, delivering a drug and also having a suction function. In another aspect, the present disclosure relates to a system comprising the stylet assembled with a bougie for guided placement of an endotracheal tube. The disclosure further relates to intubation methods in which placement of an endotracheal tube is guided with the stylet according to this disclosure.

In one aspect, this disclosure provides a stylet for use with an endotracheal tube having a lumen of an internal diameter (e), wherein the stylet is composed of a hollow tube having a length between a distal end and proximal end, wherein the stylet is bendable and shape-retaining, wherein the hollow tube has an internal diameter (d) and an external diameter (D), wherein the external diameter (D) of the hollow tube is smaller than the internal diameter (e) of the endotracheal tube and wherein the stylet is insertable into and removable from the lumen of the endotracheal tube, and wherein the hollow tube encircles a channel receiving a bougie insertable into and removable from the channel through an opening at the proximal end or at the distal end of the hollow tube.

Some preferred embodiments of the stylet include those, wherein a distal portion of the hollow tube is bent at an angle to a proximal portion of the hollow tube. In some embodiments, the hollow tube may be J-shaped. In some embodiments, the hollow tube may be a bendable and shape-retaining plastic tube. In some preferred embodiments, the external diameter of the hollow tube may be in the range from about 3 mm to about 8 mm. In some embodiments, the length of the hollow tube may be in the range from about 20 cm to about 50 cm. In some embodiments, the hollow tube may comprise an X-ray visible material. In some embodiments, the channel may further function as a suction channel and/or a drug-delivery channel. In some embodiments, the stylet may further include an inflatable or non-inflatable cuff, the cuff being attached to the stylet hollow tube and encircling the hollow tube, and the cuff being located in close proximity to the distal end of the hollow tube. In some embodiments, the stylet may further comprise a ventilator adapter having a wall encircling a lumen, the wall having a length between a distal end and a proximal end, the distal end being configured for attaching the adapter removably to the proximal end of the stylet hollow tube, and the proximal end of the adopter being configured for attaching the adapter removably to an oxygen source.

In particularly preferred embodiments, the stylet may further comprise a slip-on stopper having a tubal body slidably attachable to the hollow tube, wherein the slip-on stopper may glide along the hollow tube length in some embodiments. In some preferred embodiments, the slip-on stopper may further contain one or more flanges.

In other aspect, this disclosure provides a system comprising an endotracheal tube having a lumen and at least one stylet according to this disclosure, wherein the stylet is insertable into and removable from the lumen.

In yet another aspect, this disclosure provides a system comprising a bougie having a solid rod body, the solid rod bogy having a length (L) and at least one stylet according to this disclosure having a length (l), wherein the bougie is insertable into and removable from the channel of the stylet and wherein the length (L) of the bougie is longer than the length (l) of the stylet.

In yet another aspect, this disclosure provides a system comprising an endotracheal tube having a lumen, a bougie having a solid rod body and at least one stylet according to this disclosure, wherein the bougie is insertable into and removable from the channel of the stylet and wherein the stylet is insertable into and removable from the lumen of the endotracheal tube, and wherein a length of the bougie is longer than a length of the stylet.

In further aspects, this disclosure relates to methods for managing subject's airways, including guided intubation. Preferred intubation methods according to this disclosure may comprise one or more of the following steps:

a) positioning a bougie into the channel of the stylet according to this disclosure and advancing the distal end of the bougie from the distal end of the channel, thereby assembling a stylet/bougie device;

b) inserting the stylet/bougie device into the oral cavity and advancing the bougie through the trachea;
c) positioning an endotracheal tube over the proximal end of the stylet/bougie device and sliding the endotracheal tube over the stylet; and
d) positioning the endotracheal tube through the vocal cords.

These intubation methods may further comprise positioning a camera into the channel of the stylet and monitoring insertion and/or position of the endotracheal tube by capturing images in real time with the camera.

In yet another aspect, this disclosure relates to the use of the stylet according to this disclosure in managing subject's airways. In some embodiments, the stylet may be used

DETAILED DESCRIPTION

This disclosure relates to a stylet that can be used simultaneously with a bougie and/or other instruments, such as a camera. The stylet also contains a suction and/or drug-delivery channel. The stylet is suitable for guided insertion of an endotracheal tube and provides a technical advantage of preventing damage to an endotracheal tube during insertion, thereby helping in decreasing a number of insertion attempts needed for placement. In some embodiments, the stylet and bougie device can be used for ventilation and in other applications without an endotracheal tube.

Figure 9:
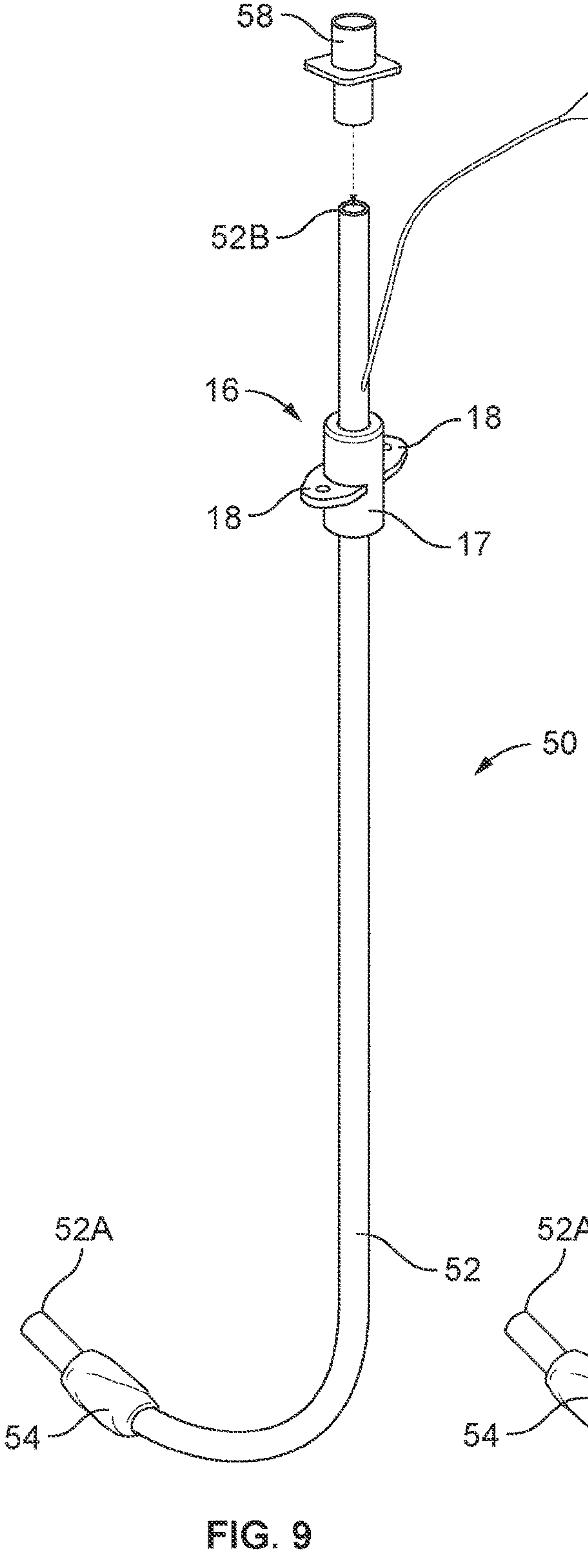
FIG. 9 is a perspective view of another embodiment for a stylet according to this disclosure and having a cuff.
Figure 10:
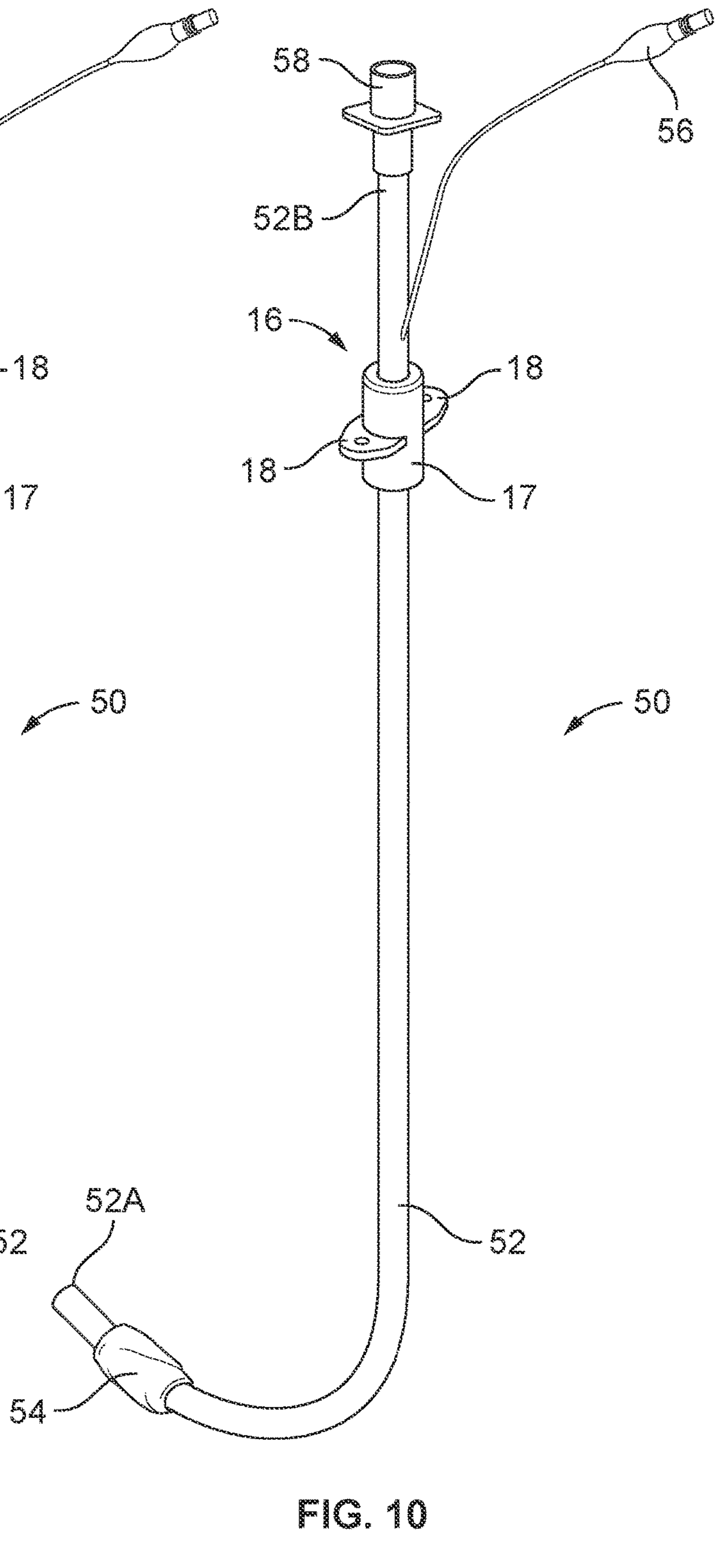
FIG. 10 is a perspective view of the stylet in FIG. 9 removably connected to a ventilator adapter.

Referring to FIGS. 1A, 1B, 2, 3, 4, 5, 6, 7 and 8, they depict one embodiment of the stylet according to this disclosure, generally 10. Referring to FIGS. 9 and 10, they depict an alternative embodiment of the stylet according to this disclosure, generally 50.

In this disclosure, the term "distal end" means the end which is introduced into a patient's oropharynx first during examination and/or in an intubation procedure. The "proximal end" is opposite to the distal end.

In preferred embodiments, the stylet 10 is a hollow tube 12 having a length between a distal end 12A and a proximal end 12B and the hollow tube 12 encircling a channel (lumen) 13 that starts with an inlet (opening) at or near the proximal end 12B of the hollow tube 12 and proceeds for at least a portion of the hollow tube 12 length and ends with an outlet (opening) at or near the distal end 12A of the hollow tube 12. In some embodiments, the hollow tube 12 contains only one channel 13. In other embodiments, the hollow tube 12 may contain one or more additional peripheral channels (not shown) that can be located in the hollow tube 12 wall and/or in alternative, the channel 13 may have a dividing wall.

The hollow tube 12 is preferably flexible, bendable and shape-retaining. Preferably, the hollow tube 12 is fabricated from a plastic material which is bendable and shape-retaining. Preferred methods of fabrication may include, but are not limited to, extrusion and plastic molding. Some preferred embodiments may include those in which the hollow tube 12 is composed of an X-Ray visible material.

Preferred stylets 10 include those in which some distal portion, e.g., ⅙, ⅕ or ¼ of the hollow tube 12 length can be bent at an angle $\alpha$ to a proximal portion, including angulation in the range from about 145 degrees to about 10 degrees, and preferably from about 90 to about 70 degrees. Some preferred stylets are J-shaped. Some preferred stylets 10 include those which are fabricated as J-shaped. In some embodiments, the hollow tube 12 is fabricated without angulation and is linear, but it can be bent prior to use and will retain the angulation because the hollow tube 12 is made of a shape-retaining material.

The length of the hollow tube 12 may vary, but typically it is compatible with a length of an endotracheal tube. Preferably, the stylet 10 has a length longer than the length of an endotracheal tube (ETT) with which the stylet 10 is to be used. Some preferred embodiments may include stylets in which the hollow tube 12 is from about 20 to about 50 cm long. However, longer or shorter stylets 10 can be also suitable, depending on application and patient's anatomy, e.g., a shorter stylet may be needed for a pediatric patient in comparison to an adult patient.

The hollow tube 12 has an internal diameter (d) and an external diameter (D). The external diameter (D) of the hollow tube 12 is smaller than an internal diameter of an endotracheal tube with which the stylet 10 is to be used. It will be appreciated that endotracheal tubes known in the art are available in different sizes. By convention, a size for an endotracheal tube is defined by its internal diameter in millimeters (mm), including 3 mm for infants, 6.0 for pediatric patients, or 7.5 to 8.0 mm or even 8 to 8.5 mm for adult patients. ETTs in other sizes can be also used.

In order for the stylet 10 to fit within the ETT lumen, the external diameter of the hollow tube 12 may be smaller than 8.5 mm, or smaller than 6 mm or even smaller than 3 mm if the stylet 10 is to be used with an ETT in an infant size. In some applications, the external diameter D of the hollow tube 12 may be in the range from about 3 mm to about 8 mm. Other diameters such as 8.5 mm, 9 mm or 2 mm may be suitable as well.

The internal diameter (d) of the hollow tube 12 is large enough for fitting a bougie 14 into the channel 13. The internal diameter (d) may be in the range from about 3 mm to about 6 mm in some applications. The internal diameter (d) may be of any size, as needed for a particular procedure and a subject's anatomy.

Figure 1B:
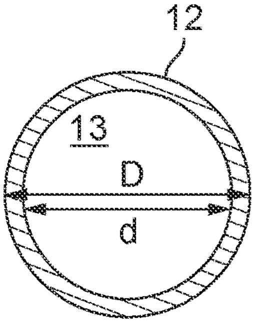
FIG. 1B is a cross-sectional view for the embodiment shown in FIG. 1A.
Figure 1A:
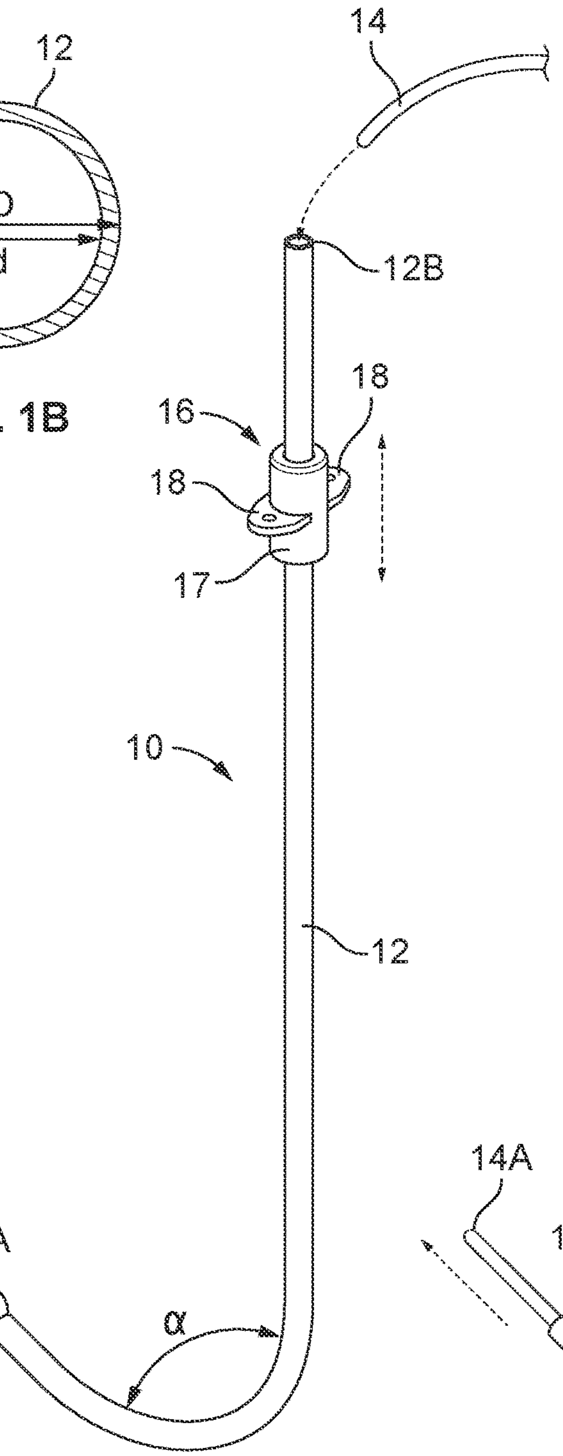
FIG. 1A is a perspective view of one embodiment of a stylet and bougie device according to this disclosure.
Figure 2:
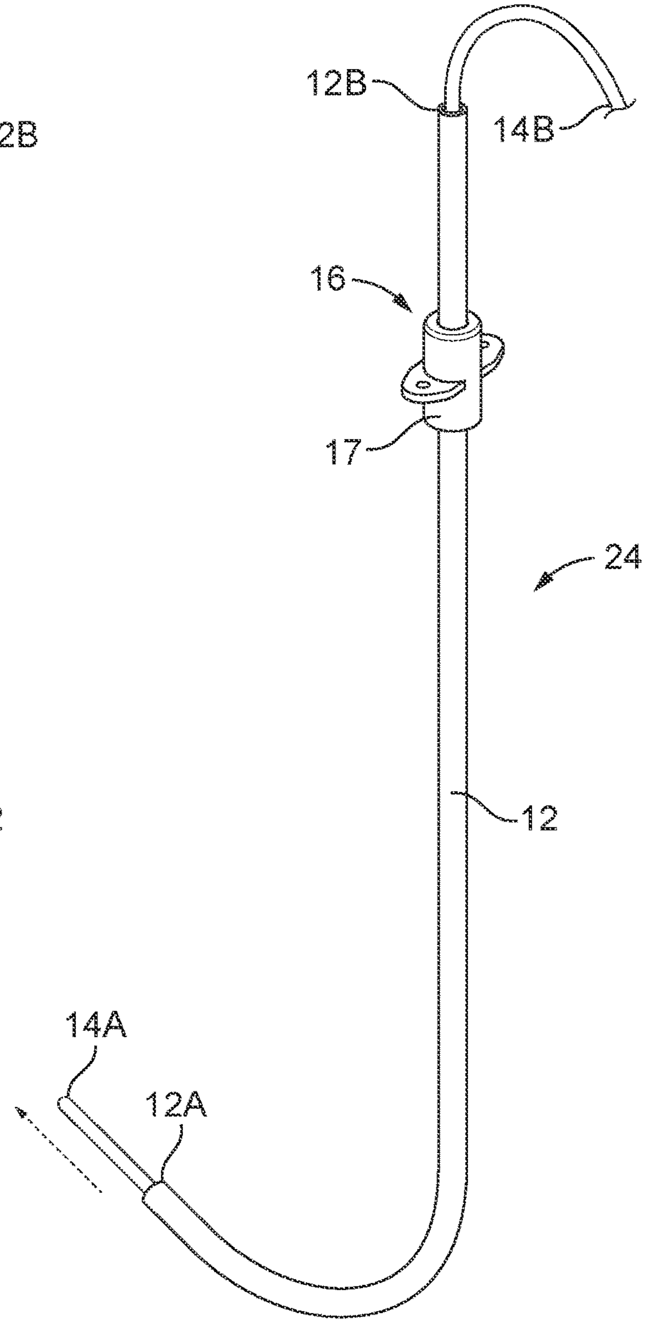
FIG. 2 is a perspective view the embodiment of FIG. 1A showing a bougie being positioned inside the stylet and extending distally from the distal end of the stylet.

As shown in FIG. 2, the bougie 14 can be assembled with the stylet 10 by inserting the bougie 14 into the channel 13 through an opening at the proximal end 12B of the hollow tube 12. The internal diameter (d) of the hollow tube 12 is larger than a diameter (B) of the bougie 14 which is preferably a solid rod having a length (L) between a distal end 14A and a proximal end 14B, such that the bougie 14 can pass through the channel 13. The length (L) of the bougie 14 is longer than a length (l) of the hollow tube 12. Because the bougie 14 is longer than the hollow tube 12, when the bougie 14 is inserted into the hollow tube 12, the distal end 14A of the bougie 14 can extend from the distal end 12A, while the proximal end 14B of the bougie 14 still remains extended from the proximal end 12B of the hollow tube 12.

The distal end 14A of the bougie 14 can extend distally through an opening at the distal end 12A of the hollow tube 12, while the proximal end 14B still remains proximal to the proximal end 12B of the hollow tube 12. As the internal diameter (d) of the hollow tube 12 is larger than a diameter (B) of the bougie 14 and a length (L) of the bougie 14 is longer than a length (l) of the hollow tube 12, a healthcare professional can manipulate the proximal end 14B of the bougie 14 which remains outside the subject's body during procedures in order to rotate the bougie 14 inside the channel 13 and/or to advance the bougie 14 along the length of the hollow tube 12 such that the distal end 14A of the bougie 14 can be moved further away or closer to the distal end 12A of the hollow tube 12 while the stylet 10 is positioned in the subject.

Preferred bougies according to this disclosure include those which are fabricated as flexible solid rods of a length (L) longer than the stylet 10. In some embodiments, the distal end 14A of the bougie 14 may be covered with a soft tip in order to minimize an injury to patient's tissues when the bougie 14 is used for guiding insertion of an ETT.

The stylet 10 according to this disclosure can be used with any conventional bougies. After the ETT is inserted, the bougie 14 can be removed from the channel 13 of the stylet 10 while the stylet 10 may remain inserted in the subject. If the bougie 14 needs to be re-inserted, this can be done expeditiously by re-introducing the bougie 14 into the channel 13 of the stylet 10 which is still in place in the subject. This provides a technical advantage over conventional stylets and conventional bougies that are use separately.

Figure 3:
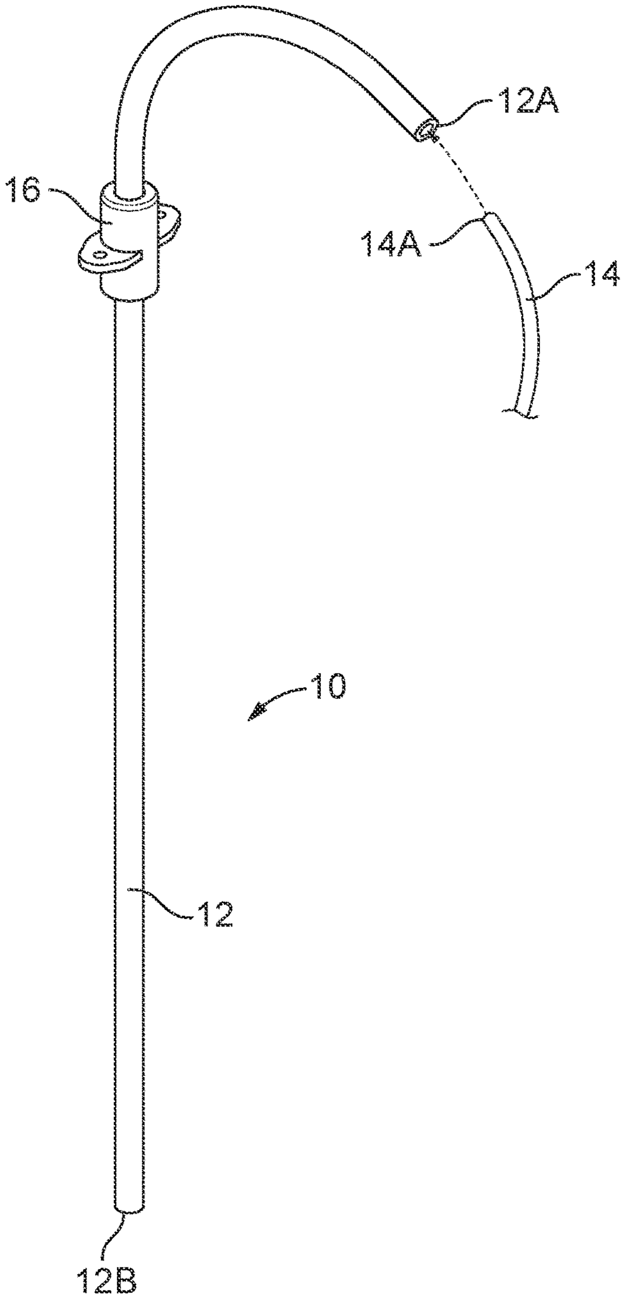
FIG. 3 is a perspective view of the embodiment of FIG. 1A showing a bougie being insertable from the distal end of the stylet.
Figure 4:
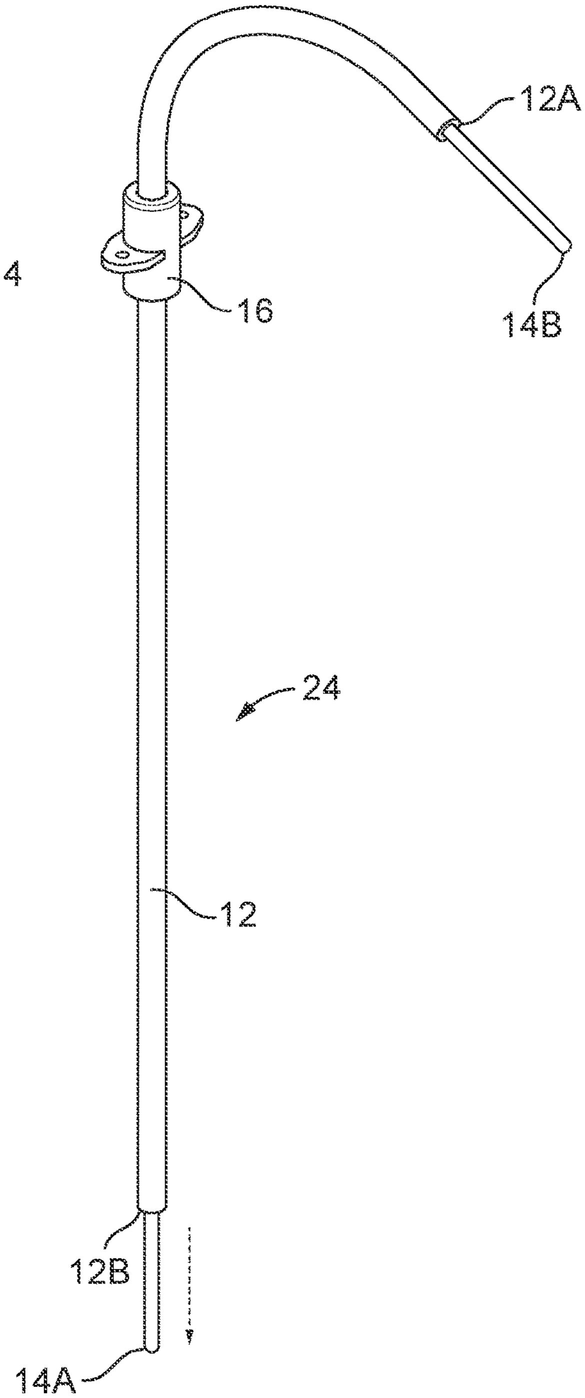
FIG. 4 is a perspective view the embodiment of FIG. 1A showing a bougie being positioned inside the stylet through the distal end and extending distally from the proximal end of the stylet.

In some embodiments and as is shown in FIG. 2, the bougie 14 can be inserted through the proximal end 12B of the hollow tube 12 such that the distal end 14A of the bougie 14 can extend from the distal end 12A of the hollow tube 12. In other embodiments and as is shown in FIGS. 3 and 4, the bougie 14 can be inserted through the distal end 12A of the hollow tube 12 such that the distal end 14A of the bougie 14 can extend distally from the proximal end 12B of the hollow tube 12. These embodiments can be useful with a J-shaped or otherwise angulated stylet when stylet's angulation is not suitable, and/or it would be preferable to utilize the proximal portion of the hollow tube 12 during ETT insertion manipulations or other procedures.

Unlike conventional stylets which are typically made from solid steel or other material with no channels, the stylet 10 according to this disclosure contains at least one channel 13 suitable for housing a bougie. Accordingly, a medical professional can manipulate a bougie while also using a stylet.

Furthermore, the channel 13 can be also used for housing a camera 18 insertable and removable into the channel 13. The camera 18 can be any videoscope or any other imaging device typically used in laryngoscopy and/or endoscopy. Suitable cameras include those which transmit real-time video images, preferably 2.0 megapixel or higher, including those with a WiFi capability and preferably compatible for wireless transmission to a smart phone, tablet and/or a computer. In alternative or in addition to wireless transmission, suitable cameras include those which can be connected to a monitor with a cable. In some embodiments, a camera can be battery-operated. Suitable cameras include a charge-coupled device (CCD) located at the distal end of the scope (wand) of the camera (not shown). Suitable cameras also include fiberscopes, and preferably fiberscopes with a probe of adjustable length.

A camera can be further equipped with a light source, the light intensity of which is preferably adjustable. When a camera is positioned in the channel 13, it can provide real-time images of the subject's glottis, larynx and/or vocal cords. Accordingly, placement of the ETT 22 or verification of its position can be performed under continuous visualization.

Other instruments, including, but not limiting, a bronchoscope 20, biopsy forceps (not shown) or a catheter (not shown) can be also housed in the channel 13, providing a technical advantage for delivering a medicament and/or removing bodily secretion without disturbing the ETT position.

Figure 8:
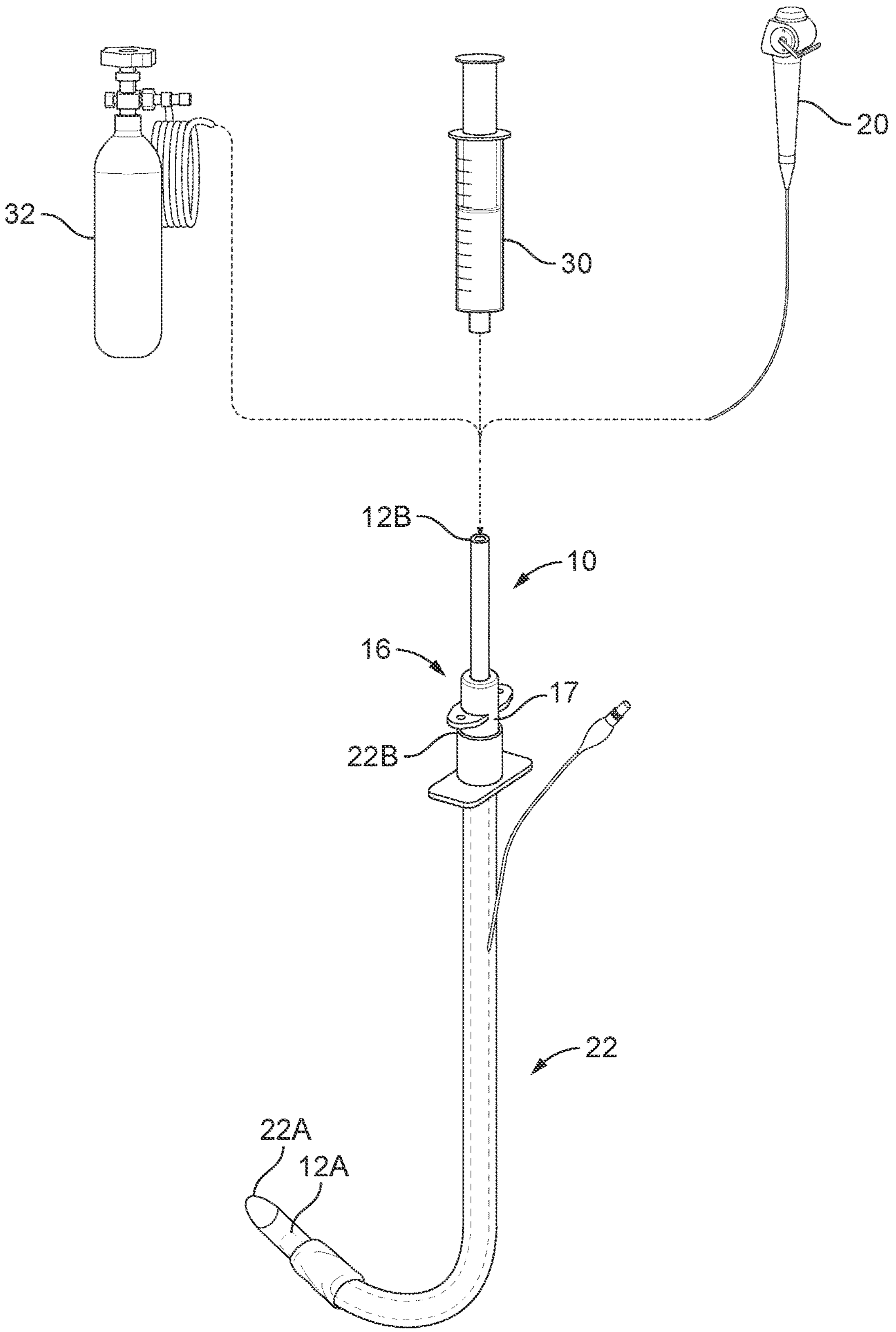
FIG. 8 is perspective view of further applications for an assembly in which the stylet is providing a backbone support to an endotracheal tube and can be also used for delivering oxygen and/or a medication and/or housing a bronchoscope.

Furthermore, and as is shown in FIG. 8, the stylets according to this disclosure have a capacity for delivering a medication, e.g., a local anesthetic, through the channel 13. This can be accomplished by connecting a syringe 30 to the proximal end 12B of the hollow tube 12. Other applications include, but are not limited to, connecting the hollow tube 12 to an oxygen source 32 for establishing air flow through the stylet 10 or connecting the hollow tube 12 to a vacuum pump if suction may be needed. Thus, unlike conventional stylets, the stylet 10 according to this disclosure contains a suction channel and a drug-delivery channel. In some embodiments, the suction channel and a drug-delivery channel can be combined in the same channel 13. In other embodiments, the stylet 10 may contain more than one channel, e.g., one central channel 13 and one or more peripheral channels, each having an inlet and an outlet and aligned along at least a portion of the hollow tube 12 length.

In some preferred embodiments, the stylet 10 comprises a slip-on stopper 16 slidably attached to the hollow tube 12. The slip-on stopper 16 can be slipped-on the hollow tube 12 and it can glide along the hollow tube 12. In some preferred embodiments, the slip-on stopper 16 is composed of a body 17 with a channel. In some embodiments, the body 17 may be substantially tubal, or cylindrical or a bead-like or conical, or the slip-on stopper 16 can be a ring, preferably with one or more flanges (not shown). The slip-on stopper 16 may be fabricated from any material suitable for obtaining a slip-on fit over the hollow tube 12. In some embodiments, the slip-on stopper 16 can be made of a plastic, rubber or even elastic fibric or other materials can be used as well.

In some preferred embodiments, the slip-on stopper 16 contains one or more flanges 18 attached to the external wall of the body 17. The one or more flanges 18 may extend perpendicular or substantially perpendicular to the external wall of the body 17.

In some embodiments, the slip-on stopper 16 has an internal diameter (t) the same or somewhat larger than the external diameter (D) of the hollow tube 12 such that the slip-on stopper 16 can be slipped on the hollow tube 12. If the slip-on stopper 16 is made of a stretchable material, then the slip-on stopper 16 can be stretched to the diameter (t) such that the slip-on stopper 16 fits over the hollow tube 12.

The slip-on stopper 16 can then be moved along the hollow tube 12 such that a position of the slip-on stopper 16 relative to the proximal end 12B of the hollow tube 12 can be adjusted. Accordingly, a position of the slip-on stopper 16 on the hollow tube 12 can be adjusted by moving the slip-on stopper 16 closer or further away from the proximal end 12B of the hollow tube 12. When not in use, the slip-on stopper 16 can be completely separated from the hollow tube 12 and removed in some embodiments.

Figure 5:
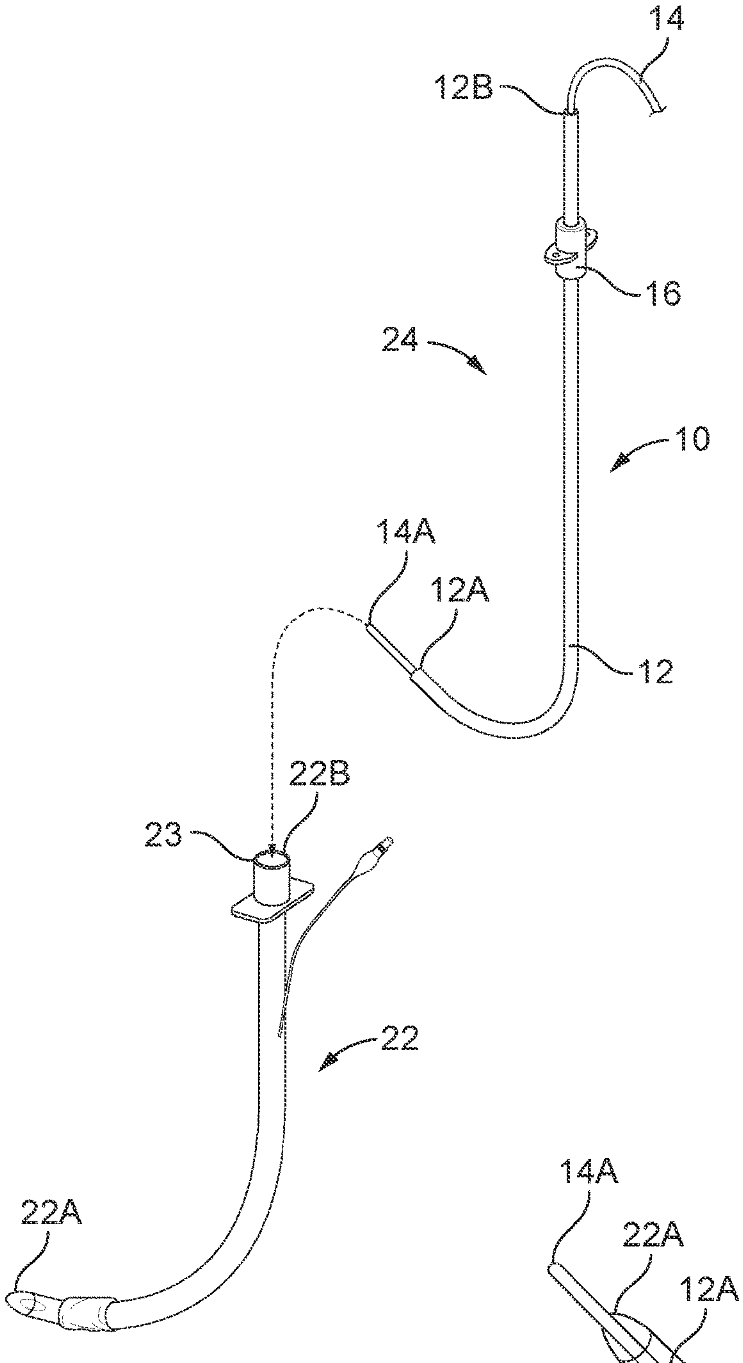
FIG. 5 is a perspective view of one embodiments of the stylet and bougie device being assembled with an endotracheal tube (ETT).

As shown FIGS. 5, 6, 7 and 8, the stylet 10 can be used in a system with an endotracheal tube 22, one embodiment of which is shown in FIG. 5. In some other embodiments, the stylet 10 can be used in procedures without an endotracheal tube.

The endotracheal tube (ETT) 22 is a hollow tube with a distal end 22A and a proximal end 22B, containing a lumen 23 that can be used for ventilating a patient after the endotracheal tube 22 has been positioned in the trachea and through the vocal cords. While in the embodiment of FIGS. 5-8, a single lumen ETT is shown, double-lumen ETTs are also suitable for use with the stylet 10.

Figure 6:
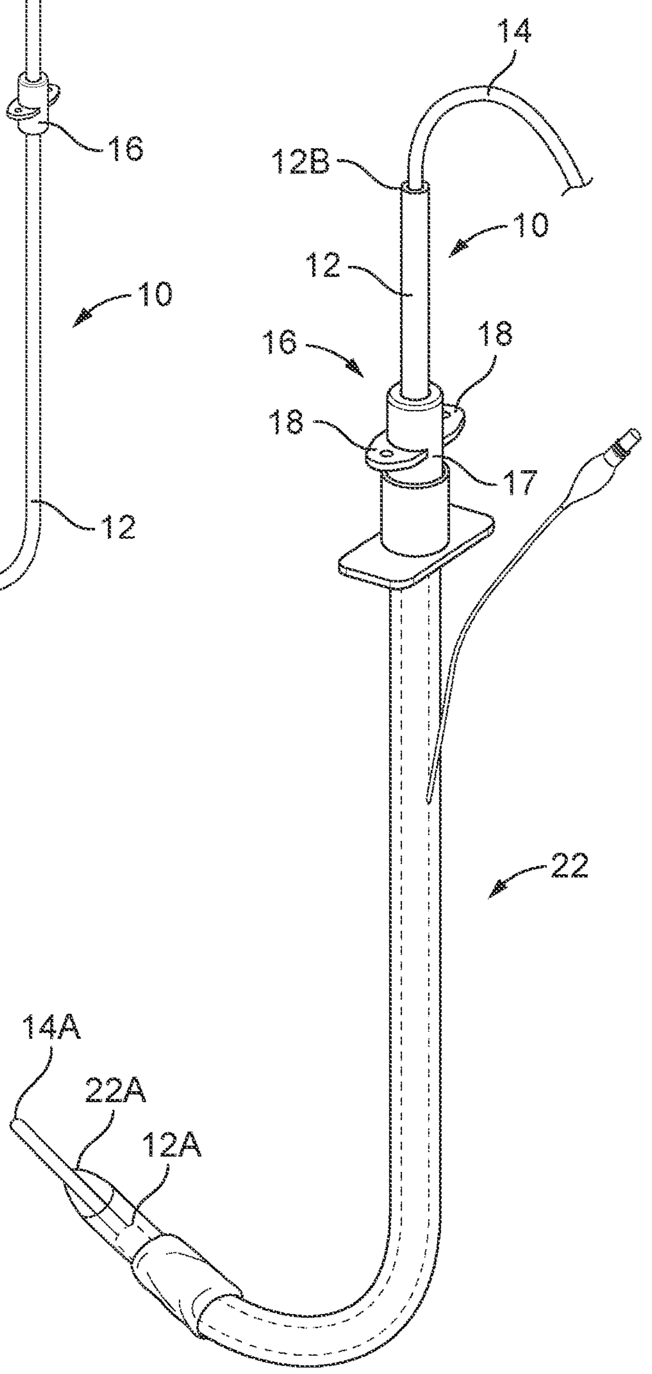
FIG. 6 is a perspective view of the assembly of FIG. 5 showing the stylet and bougie device being positioned in the ETT lumen, and a position of the stylet in the ETT lumen being secured with a flanged stopper.

In an embodiment of the system shown in FIGS. 5 and 6, the stylet 10 is combined with the bougie 14 by inserting the bougie 14 into the channel 13 of the hollow tube 12. The distal end 14A of the bougie 14 can extend distally from the distal end 12A of the stylet 10.

The stylet/bougie device, generally 24, is inserted into the lumen 23 of the endotracheal tube 22. The distal end 12A of the stylet 10 is adjusted inside the lumen 23 such that the distal end 12A of the stylet 10 remains positioned inside the lumen 23 of the endotracheal tube 22 such that the distal end 12A is near the distal end 22A of the ETT 22. The distal end 14A of the bougie 14 extends distally from the distal end 22A of the ETT 22. A position of the bougie 14 is also adjusted such that the distal end 14A of the bougie 14 extends distally from the distal end 22A of the endotracheal tube 22.

During adjustments, the slip-on stopper 16 remains proximal to the proximal end 22B of the ETT 22. The position of the slip-on stopper 16 on the hollow tube 12 can be further adjusted by sliding the slip-on stopper 16 on the hollow tube 12.

After a healthcare professional finalizes the relative position of the stylet 10 inside the lumen 23 of the ETT 22, the slip-on stopper 16 can be brought into the contact with the proximal end 22B of the ETT 22. In preferred embodiments, the external diameter (T) of the slip-on stopper 16 is such that the stopper 16 fits tightly with the internal diameter of the ETT 22 such that the slip-on stopper 16 prevents air leakage from the lumen 23 when the lumen 23 is used for ventilation.

Thus, the slip-on stopper 16 has a double function—it functions as a stopper for an endotracheal tube (ETT) 22 and it also holds the stylet 10 in place relative to the ETT 22, preventing the stylet 10 from sliding distally when the stylet 10 is in use in the endotracheal tube 22.

In the embodiments where the slip-on stopper 16 has one or more flanges 18, the one or more flanges 18 extend over the lumen 23. The flanges 18 secure the stylet 10 further in place and prevent the stylet 10 from sliding distally into the ETT 22.

While the stylet 10 is secured with the slip-on stopper 16 and it is prevented from sliding distally into the ETT 22, the bougie 14 can move distally unconstrained. This provides a further technical advantage for a healthcare professional who can manipulate the bougie 14 and the endotracheal tube 22 with one hand, if needed.

This system may help with expeditious positioning of the ETT 22 wherein the ETT 22 is constantly guided with the bougie 14, while the stylet 10 provides the backbone and structure to the ETT 22 which is otherwise flexible. Because the stylet 10 combines the bougie 14 and ETT 22 into one system, a further technical advantage is that it is less likely that the bougie 14 would be separated from the ETT 22 during insertion and/or that the ETT 22 would be damaged during insertion, and also minimizing a number of insertion attempts.

Figure 7:
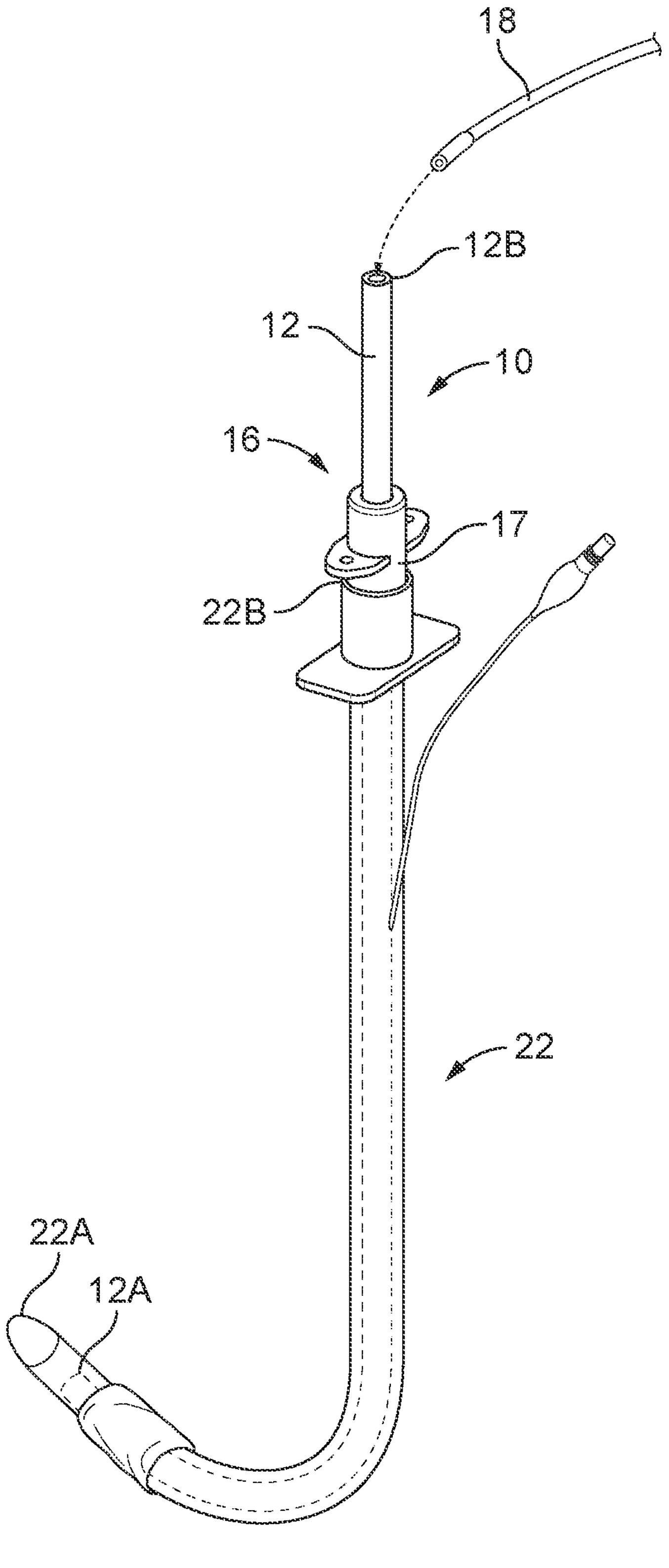
FIG. 7 is a perspective view of an assembly in which the stylet is secured in the ETT lumen with a flanged stopper, the bougie is removed and a camera being inserted into the stylet channel.

If/when the bougie 14 is no longer in use, the bougie 14 can be removed from the stylet 10, while the stylet 10 may remain positioned in the ETT 22, as shown for example, in FIGS. 7 and 8. The channel 13 of the stylet 10 can be also used for positioning a camera, delivering a medication, performing suction and/or some other procedures while the endotracheal tube 22 remains in place and undisturbed.

In some embodiments (not shown), the stylet 10 may further comprise an outer sheath, wherein the stylet 10 is insertable into and removable from the sheath. The outer sheath has a hollow tubal body formed by a wall encircling a lumen, the wall having a longitudinal length between a distal end and a proximal end, preferably the length being in the range from about 10 cm to about 50 cm. The hollow tubal body has an opening at or near the distal end and an opening at or the proximal end, both openings in communication with the lumen. A cross-sectional diameter of the hollow tubal body of the sheath is larger than an external diameter (D) of the stylet 10, but smaller than a diameter (e) of an endotracheal tube 22, such that the stylet 10 fits inside the sheath lumen and the sheath can fit into the ETT lumen.

The stylet 10 is insertable into and removable from the lumen of the sheath. The sheath can be made from various plastic materials, and preferably the sheath is made of a flexible plastic material. In use, the stylet 10 can be placed into the sheath, preferably a camera can be positioned in the channel 13 for monitoring insertion into the trachea. After the insertion is completed, the stylet 10 and/or camera may be removed, while the sheath remains positioned in the trachea. An endotracheal tube 22 can be then placed over the proximal end of the sheath, and inserted into trachea, while the sheath guides the positioning of the endotracheal tube through the trachea.

Referring to FIGS. 9 and 10, the present disclosure provides an alternative embodiment of a stylet, generally 50. The stylet 50 is composed of the same elements as the stylet 10 in that it is a hollow tube 52 having a length between a distal end 52A and a proximal end 52B, the hollow tube 52 encircling a channel (lumen, not shown) that starts with an inlet (opening) at or near the proximal end 52B of the hollow tube 52 and proceeds for at least a portion of the hollow tube 52 length and ends with an outlet (opening) at or near the distal end 52A of the hollow tube 52. In some embodiments, the hollow tube 52 contains only one channel. In other embodiments, the hollow tube 52 may contain one or more additional peripheral channels (not shown) that can be located in the hollow tube 52 wall and/or in alternative, the channel may have a dividing wall.

In contrast to the stylet 10, the stylet 50 further comprises a cuff 54 that wraps around the hollow tube 12 and is preferably attached to the hollow tube 12. The cuff 54 is located proximally to the distal end 12A of the hollow tube 12. Preferably, the cuff 54 is inflatable, even as soft non-inflatable cuffs can be also used in some embodiments. In those preferred embodiments where the cuff 54 is inflatable, the cuff 54 is connected to means 56 which can be used for inflating the cuff 54.

The stylet 10 or the stylet 50 may be fitted with a removable ventilator adapter 58 having a wall encircling a lumen, the wall having a length between a distal end and a proximal end, the distal end being configured for attaching the adapter removably, as shown for example, in FIGS. 9 and 10 to the proximal end 52B of the stylet hollow tube 52, and the proximal end of the ventilator adapter 58 being configured for removably attaching the adapter 52 to an oxygen source. The ventilator adapter 58 can be used as a conduit for removably connecting the stylet 50 to an oxygen source (not shown).

The stylet 50 can be used for ventilating a patient without an endotracheal tube. The stylet 50 can be positioned in the trachea, preferably with a guidance of a bougie 14. After the proper positioning of the stylet is verified, the bougie 14 is removed from the hollow tube 52 and the hollow tube 52 is connected to the ventilator adapter 58. The cuff 54 is inflated with means 56 in embodiments with an inflatable cuff. The ventilator adapter 58 is connected to an oxygen source and ventilation can take place through the hollow tube 52 of the stylet 50.

In yet another aspect, the present disclosure provides intubation methods in which one or more systems according to this disclosure are used for guided placement of an ETT. These methods may comprise:

a) inserting the bougie 14 into the channel 13 of the stylet 10 such that the distal end 14A of the bougie 14 extends distally from the distal end 12A of the hollow tube 12 or such that the distal end 14A of the bougie 14 extends distally from the proximal end 12B of the hollow tube 12, and thereby assembling the stylet/bougie device 24;

b) positioning the stylet/bougie device 24 in the subject's trachea, c) inserting the proximal end 14B of the bougie 14 and the proximal end 12B of the stylet 12 into the distal end opening 22A of an endotracheal tube 22 and sliding the endotracheal tube 22 over the stylet/bougie device 24 such that the distal end 12A of the stylet 10 is positioned proximally to the distal end 22A of the endotracheal tube 22;

d) optionally securing the position of the stylet 10 relative to the endotracheal tube 22 by bringing the slip-on stopper 16 into a contact with the proximal end 22B of the endotracheal tube 22; and e) extending the distal end 14A of the bougie 14 from the distal end 22A of the endotracheal tube 22 and guiding placement of the endotracheal tube 22 through the trachea with the bougie 14.

Further methods may include using the stylet 50 having a cuff according to this disclosure for ventilating a patient or other procedures without an endotracheal tube.

Various methods can be used for manufacturing the stylets according to this disclosure. In some preferred embodiments, the stylets are made from a plastic polymer, e.g., a polypropylene-based blend formulated such that the material is shape-retaining after it is molded. The material can be extruded and/or molded into a hollow tube of the predetermined diameter and cut to a required length. If needed, the stylet can be bent into a J-shape, for example, during the molding.

From the foregoing description, all objections of the present invention are realized. A stylet having a channel for housing a bougie, the stylet preferably also including a slip-on stopper slidably attached to the stylet, systems comprising the stylet, methods of their use, and manufacturing methods have been described.

What is claimed is:

1. A stylet for use with an endotracheal tube having a lumen of an internal diameter (e), the stylet comprising a bendable and shape-retaining hollow plastic tube having a length (1) between a distal end and proximal end, wherein when in use and bent at an angle prior to placement in a subject, the hollow plastic tube retains the shape into which it has been bent, wherein the hollow tube has an internal diameter (d) and an external diameter (D), wherein the external diameter (D) of the hollow tube is smaller than the internal diameter (e) of the endotracheal tube and wherein the stylet is insertable into and removable from the lumen of the endotracheal tube, wherein the hollow tube encircles a channel being configured for receiving a bougie insertable into and removable from the channel through an opening at the proximal end or distal end of the hollow tube and the channel being further configured for housing a camera insertable into and removable from the channel; and wherein the stylet is bendable and shape-retaining.

2. The stylet of claim 1, wherein a distal portion of the hollow tube is bent at an angle to a proximal portion of the hollow tube.

3. The stylet of claim 1, wherein the hollow tube is J-shaped.

4. The stylet of claim 1, wherein the external diameter of the hollow tube is in the range from about 3 mm to about 8 mm.

5. The stylet of claim 1, wherein the length of the hollow tube is in the range from about 20 cm to about 50 cm.

6. The stylet of claim 1, wherein a length of the bougie is longer than the length of the stylet.

7. The stylet of claim 1, wherein the hollow tube comprises an X-ray visible material.

8. The stylet of claim 1, wherein the channel is a suction channel and/or a drug-delivery channel.

9. The stylet of claim 1, wherein the stylet further comprises a slip-on stopper having a tubal body slidably attachable to the hollow tube, wherein the slip-on stopper is configured for gliding along the hollow tube length.

10. The stylet of claim 9, wherein the slip-on stopper contains one or more flanges.

11. The stylet of claim 1, wherein the stylet further has a cuff, the cuff being attached to the stylet hollow tube and encircling the hollow tube in close proximity to the distal end of the hollow tube.

12. The stylet of claim 11, wherein the cuff is inflatable.

13. A method for providing oxygen to a subject, the method comprising:

positioning the stylet of claim 12 in the subject's trachea, inflating the cuff, connecting the proximal end of the stylet to an oxygen source; and starting an oxygen flow from the oxygen source through the stylet to the subject.

14. The stylet of claim 1, wherein the stylet further comprises a ventilator adapter having a wall encircling a lumen, the wall having a length between a distal end and a proximal end, the distal end being configured for attaching the adapter removably to the proximal end of the stylet hollow tube, and the proximal end of the adopter being configured for attaching the adapter removably to an oxygen source.

15. A system comprising an endotracheal tube having a lumen and the stylet claim 1, wherein the stylet is insertable into and removable from the lumen.

16. A system comprising a bougie having a solid rod body and the stylet of claim 1, wherein the bougie is insertable into and removable from the channel of the stylet, and wherein the bougie solid rod body has a length (L) longer than the length (l) of the hollow tube.

17. A system comprising an endotracheal tube having a lumen, a bougie having a solid rod body and the stylet of claim 1, wherein the bougie is insertable into and removable from the channel of the stylet and wherein the stylet is insertable into and removable from the lumen of the endotracheal tube.

18. An intubation method comprising:

(a) positioning a bougie into the channel of the stylet of claim 1 and advancing the distal end of the bougie from the distal end of the channel, thereby assembling a stylet/bougie device;

(b) inserting the stylet/bougie device into the oral cavity and advancing the bougie through the trachea;

(c) positioning an endotracheal tube over the proximal end of the stylet/bougie device and sliding the endotracheal tube over the stylet; and (d) positioning of the endotracheal tube through the vocal cords.

19. The intubation method of claim 18, wherein the method further comprises positioning a camera into the channel of the stylet and monitoring an insertion method and/or a position of the endotracheal tube in the trachea by capturing images in real time with the camera.

* * * * *